United States Patent [19]

Shibuya et al.

[11] Patent Number: 4,886,822
[45] Date of Patent: Dec. 12, 1989

[54] SUBSTITUTED ANILIDE COMPOUNDS WHICH ARE USEFUL IN THE TREATMENT OF ARRHYTHMIA

[75] Inventors: Kimiyuki Shibuya; Yoshio Takahashi, both of Higashimurayama; Seiichi Sato, Tokyo; Hiromichi Shigyo, Fuchu; Tomio Ohta, Sayama; Yasumi Uchida, Ichikawa, all of Japan

[73] Assignee: Kowa Company, Ltd., Aichi, Japan

[21] Appl. No.: 179,218

[22] Filed: Apr. 8, 1988

[30] Foreign Application Priority Data

Apr. 10, 1987 [JP] Japan .................................. 62-87021

[51] Int. Cl.⁴ .................... C07D 213/54; A61K 31/44
[52] U.S. Cl. ...................................... 514/357; 546/337
[58] Field of Search ......................... 546/337; 514/357

[56] References Cited

U.S. PATENT DOCUMENTS 3,449,349 6/1969 Shen et al. ........................... 546/337
4,376,775 3/1983 Lesher et al. ....................... 514/346

OTHER PUBLICATIONS

Chemical Abstracts, vol. 87, No. 7, Abstract 53,093k, p. 453, Aug. 15, 1977.

Primary Examiner—Mary C. Lee
Assistant Examiner—Zinna Northington-Davis
Attorney, Agent, or Firm—Wenderoth, Lind & Ponack

[57] ABSTRACT

A substituted anilide derivative of the formula

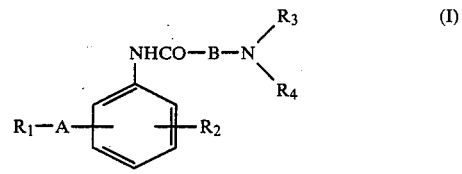

wherein $R_1$ represents a mononuclear or binuclear heterocyclic group which contains 1 to 3 nitrogen atoms as ring members and may have a substituent.

A represents a single bond, a carbonyl group, a sulfur atom, or a lower alkylene group which may be substituted by a hydroxyl group, $R_2$ represents a hydrogen atom, a halogen atom, a lower alkyl group, a trifluoromethyl group, a lower alkenyloxy group, or a $C_1$-$C_{14}$ alkoxy group which may have a substituent, $R_3$ and $R_4$ are identical or different, and each represents a hydrogen atom, a lower alkyl group, a phenyl group, or a phenyl(lower alkyl) group which may have a substitutent, or taken together, may form a saturated nitrogen-containing heterocyclic group together with the nitrogen atom to which they are bonded, and B represents a single bond or a lower alkylene group which may have a substituent, or an acid addition salt thereof. The compound of formula (I) or a pharmaceutically acceptable acid addition salt thereof is useful for the manufacture of antiarrhythmically active medicaments.

12 Claims, No Drawings

SUBSTITUTED ANILIDE COMPOUNDS WHICH ARE USEFUL IN THE TREATMENT OF ARRHYTHMIA

This invention relates to novel substituted anilide derivatives which have useful pharmacological activity as drugs for treating diseases of the circulatory system, particularly arrhythmia; a process for production thereof; and use thereof for treating said diseases.

Compounds having antiarrhythmic activity have previously been known. For example, West German Patent No. 2,235,745 discloses "Tocainide" represented by the following formula.

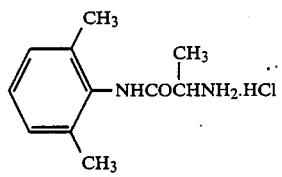

U.S. Pat. No. 2,441,498 discloses "Lidocaine" represented by the following formula.

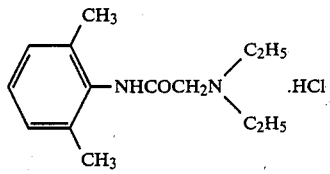

U.S. Pat. No. 3,659,019 discloses "Mexiletine" of the following formula.

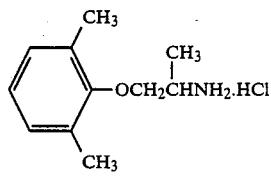

U.S. Pat. Nos. 3,900,481 and 4,005,209 disclose "Flecanide" represented by the following formula.

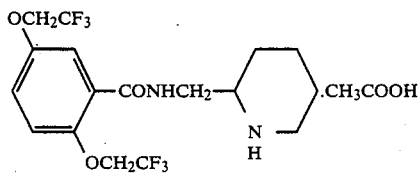

Disopyramide and procainamide are also known as anti-arrhythmic agents.

These known compounds having anti-arrhythmic activity generally tend to show undesirable actions including side effects on the central nervous system. For example, disopyramide has side effects considered to be due to its anticholinergic activity, such as thirst, ischurin, constipation, dizziness and vomiting. Since it also has an inhibiting action on the myocardium, care must be taken in its administration. Procainamide is known to induce side effects such as anticholinergic activity, cardiodepressive action, and hypotension. It has been reported that mexiletine cause side effects on the digestive system and the meuropsychotic system with a high frequency, and has activity on the central nervous system.

The present inventors have made extensive investigations for anti-arrhythmic activity free from these undesirable actions, and have finally discovered a certain type of novel substituted anilide derivatives.

According to this invention, there is provided a substituted anilide derivative of the formula

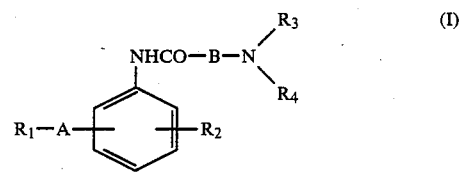

wherein
$R_1$ represents a mononuclear or binuclear heterocyclic group which contains 1 to 3 nitrogen atoms as ring members and may have a substituent, A represents a single bond, a carbonyl group, a sulfur atom, or a lower alkylene group which may be substituted by a hydroxyl group, $R_2$ represents a hydrogen atom, a halogen atom, a lower alkyl group, a trifluoromethyl group, a lower alkenyloxy group, or a $C_1$–$C_{14}$ alkoxy group which may have a substituent, $R_3$ and $R_4$ are identical or different, and each represents a hydrogen atom, a lower alkyl group, a phenyl group, or a phenyl(lower alkyl) group which may have a substituent, or taken together, may form a saturated nitrogen-containing heterocyclic group together with the nitrogen atom to which they are bonded, and B represents a single bond or a lower alkylene group which may have a substituent,
or an acid addition salt thereof.

It is found that the novel compounds of formula (I) exhibit an excellent pharmacological efficacy for the treatment of cardiovascular diseases, particularly arrhythmia, with markedly reduced side effects on the central nervous system. It has also been found that the novel compounds of this invention show different pharmacological actions from conventional analogous compounds, particularly vasoactive pharmacological activity, are useful for the treatment of arrhythmia, have low toxicity, and can be used over an extended period of time.

In the present specification and the appended claims, the term "lower" used to qualify a group or a compound means that the group or compound so qualified has not more than 6, preferably not more than 4, carbon atoms.

The "mononuclear or binuclear heterocyclic group which contains 1 to 3 nitrogen atoms as ring members and may have a substituent" in formula (I) given above includes mononuclear or binuclear heterocyclic groups which contains 1 to 3 nitrogen atoms as ring members and are 3- to 10-membered, preferably 5- to 9-membered. Preferably the heterocyclic groups are aromatic, and include, for example, pyridyl, imidazolyl, imidazopyridyl and indolyl groups, especially preferred being 2-, 3- or 4-pyridyl group, above all the 2- or 3-pyridyl group. These nitrogen-containing heterocyclic groups may be in an oxidized state, namely an N-oxide. Examples of the substituent which may exist on the heterocyclic group include lower alkoxycarbonyl groups such as methoxycarbonyl and ethoxycarbonyl; nitroxy-lower alkyl-aminocarbonyl groups such as nitroxyethylaminocarbonyl; lower alkylaminocarbonyl groups such as methylaminocarbonyl, ethylaminocarbonyl, propylaminocarbonyl, isopropylaminocarbonyl and hexylaminocarbonyl groups, lower alkylthio groups such as methylthio and ethylthio; and lower alkylsulfinyl groups such as methylsulfinyl and ethylsulfinyl. Desirably, only one such substituent exists on the heterocycle. Generally, the heterocyclic group is preferably unsubstituted, and therefore, $R_1$ is especially preferably a pyridyl group.

The bridging member A represents a single bond, a lower alkylene group which may be substituted by hydroxyl such as

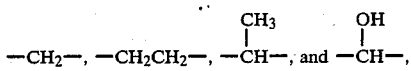

a carbonyl group or a sulfur group. The signal bond is preferred.

The "halogen atom" in the definition of the group $R_2$ includes fluorine, chlorine, bromine and iodine atoms. The "lower alkenyloxy group" is preferably an allyloxy group. The alkoxy group in the "$C_1$-$C_{14}$ alkoxy group which may have a substituent" may be linear or branched, and is preferably a lower alkoxy group. Examples of the substituent are halogen atoms such as fluorine, an amino group, and lower alkoxycarbonyl groups such as methoxycarbonyl and ethoxycarbonyl. Specific examples of the $C_1$-$C_{14}$ alkoxy group having such a substituent include methoxy, ethoxy, propoxy, isopropoxy, butoxy, 4-methyl-1-pentyloxy, octyloxy, tetradecyloxy, 2,2,2-trifluoroethoxy and ethoxycarbonylmethoxy. Generally, the group $R_2$ is preferably a lower alkyl group, an allyloxy group, a lower alkoxy group or a 2,2,2-trifluoroethoxy group, the lower alkoxy groups being especially preferred. Examples of the substituent on the phenyl group in the "phenyl(lower alkyl) group which may have a substituent" include lower alkoxy groups, a nitro group, halogen atoms and a trifluoromethyl group. Examples of the phenyl(lower alkyl) group which may have a substituent are benzyl, phenethyl, and 3,4,5-trimethoxyphenylethyl. The saturated nitrogen-containing heterocyclic group which may be formed of $R_3$ and $R_4$ together with the nitrogen atom to which they are bonded is generally 4- to 7-membered, especially 5- or 6-membered, and may be, for example, pyrrolidino and piperidino. Thus, the moiety

preferably represents an amino group, a di(lower alkyl)amino group, a phenylamino group or a (lower alkoxy-substituted phenyl)lower alkyl group, or a saturated nitrogen-containing 4- to 7-membered, especially 5- or 6-membered, heterocyclic group, especially a piperidino group. The amino group is especially preferred.

The bridging member B represents a single bond or a linear or branched lower alkylene group which may have a substituent, for example a phenyl group that may be substituted by 1 to 3 lower alkoxy groups. Linear or branched lower alkylene groups, such as —CH$_2$—, —CH$_2$—,

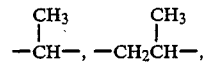

and —CH$_2$CH$_2$CH$_2$—. The group

is especially preferred.

Generally, the group $R_1$—A— and $R_2$— exist at the ortho- or meta-position to the group

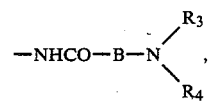

and the group $R_1$—A— exists at the para-position to the group $R_2$—.

The compounds of formula (I) may be in the form of acid addition salts. Examples of the salts includes salts of inorganic acids such as hydrochloric acid, sulfuric acid and phosphoric acid and salts of organic acids such as oxalic acid, tartaric acid, maleic acid, citric acid, fumaric acid, acetic acid, propionic acid, methanesulfonic acid and toluenesulfonic acid.

The compound of formula (I) provided by this invention can be produced, for example, by reacting an aniline derivative of the formula

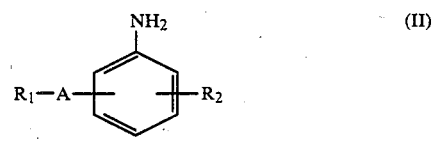

wherein $R_1$, A and $R_2$ are as defined above, with an aminoalkylcarboxylic acid of the formula

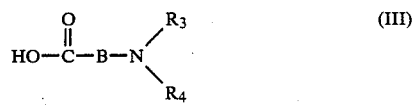

wherein $R_3$, $R_4$ and B are as defined above, or its reactive derivative.

The reaction can carried out in a conventional manner by contacting the compound of formula (II) with the compound of formula (III) in an inert organic solvent such as methylene chloride or tetrahydrofuran. The reaction temperature and time can be properly chosen. The amounts of the compound of formula (II) and the compound of formula (III) can be properly selected, and, for example, the compound of formula (III) may be used in an amount of about 1 to about 3 moles per mole of the compound of formula (II).

The compound of formula (II) used as a starting material is a known compound, or can be prepared by a known method. For example, a compound of formula (II) in which A is a single bond and $R_1$ is a pyridyl group can be obtained by reducing a nitrophenylpyridine (see J. Chem. Soc. 1943, 406–413). A compound of formula (II) in which $R_1$ is an imidazolyl or imidazopyridyl group can be obtained, for example, by reacting nitrobenzaldehyde with glyoxal and ammonia or ammonium carbonate, or by first reacting it with diaminopyridine and reducing the nitro group of the product.

A compound of formula (II) in which A is a carbonyl group can be produced, for example, by reacting a nicotinic halide or 2,3-pyridinedicarboxylic acid with a substituted benzene and subjecting the resulting nicotinoylbenzene derivative to nitration and reduction in a customary manner.

A compound of formula (II) in which A is a lower alkyl group that may have a hydroxyl group can be produced by nitrating a compound produced in accordance with the method described in Tetrahedron Letters, Vol. 22, No. 41, pages 4093–4096, such as bromobenzyl pyridine, and reducing the resulting product.

A compound of formula (II) in which A is a sulfur atom can be produced by nitrating phenylthiopyridine obtained, for example, by reacting mercaptopyridine with a halogenobenzene, and reducing the resulting product.

On the other hand, the compound of formula (III) is either a known compound, or may be easily produced by a known method. The reactive derivative of the compound of formula (III) may be a reactive derivative of a carboxylic acid known in the field of peptide chemistry, for example, halides (e.g., chlorides) and active esters of carboxylic acids.

When in the compound of formula (III), $R_3$ and $R_4$ are both hydrogen atoms, it is preferably protected with a suitable protective group (e.g., a butoxycarbonyl or trifluoroacetyl) for the amino group prior to reaction with the compound of formula (II).

A compound of formula (I) in which A is a lower alkyl group which may have a hydroxyl group can also be produced by reducing a compound of formula (I) in which A is a carbonyl group.

The compound of formula (I) so produced can be converted to its acid addition salt by contacting it with an inorganic or organic acid. The reaction may be carried out by contacting the compound of formula (I) with an inorganic or organic acid in the presence or absence of a solvent. The reaction temperature and time can be properly selected. For example, temperatures from room temperature to about 50° C. and periods of 1 to 24 hours may be employed. Examples of the inorganic or organic acids may be those already exemplified hereinabove with regard to the acid addition salts.

The compounds of formula (I) and the pharmaceutically acceptable acid addition salts thereof have reduced side effects on the central nervous system as compared with conventional analogous compounds and exhibit vasoactive pharmacological activity which the conventional compounds do not. For this reason, they are useful for treating arrhythmic and can be used for an extended period of time. Furthermore, they have low toxicity.

Animal tests shown below demonstrate the excellent anti-arrhythmic activity of the compounds of formula (I) provided by this invention.

Test Example 1

Activity on Chloroform-Induced Arrhythmia:

ICR-strain mice having a body weight of 20 to 35 g (10 per group) were used, and the test compound was administered orally in a dose of 30 mg/kg. The mice were put in a 1-liter beaker, and observed for 20 minutes for their symptoms or conditions. Then, they were placed in a vessel saturated with a vapor of chloroform, and the time which elapsed until the animals ceased to breathe was measured. After the stopping of the breathing, the mice were taken out from the vessel and their cardiograms (second induction) were recorded by a memory oscilloscope (VC-10, made by Nippon Kodensha) and a linear corder ($WTR_{331}$ made by Watanabe Measuring Instrument Co., Ltd.). The occurrence of ventricular fibrillation (VF) was evaluated by the cardiograms. The results are shown in Table 1 by percent VF inhibition.

TABLE 1

| Test compound (*) | Percent VF inhibition (%) |
|---|---|
| 1 | 80 |
| 8 | 90 |
| 20 | 100 |
| 23 | 70 |
| 28 | 70 |
| 30 | 70 |
| 33 | 80 |
| free form of 33 | 100 |
| 45 | 80 |
| 46 | 80 |
| 56 | 70 |
| mexiletine | 50 |

(*) The numbers correspond to those of Examples given hereinbelow.

Test Example 2

Activity on Ouabain-Induced Arrhythmia:

Male hybrid adult dogs weighing 9 to 17 kg were anaesthetized, and fixed in the supine position under artificial respiration. The blood pressures, heart rates and second induced cardiograms (using RA-101 made by San-ei Measuring Instrument Co., Ltd.) of the animals were measured. Ouabain was first intravenously administered in a dose of 40 μg/kg, and 30 minutes later in a dose of 20 μg/kg. Furthermore, until continuous ventricular arrhythmia was obtained, 10 μg/kg of ouabain was cumulatively administered at intervals of 15 minutes. The ventricular automaticity was examined substantially in accordance with the method of Roberts et al. (J. Pharmacol. Exp. Ther. 117, 374–384, 1956). The peripheral end of the right cervical vagus nerve was stimulated with short waves (0.4–1.9 V, 1 millisecond, 20 Hz) using an electrical stimulating device (MSE-3R made by Nippon Kodensha) for 10 seconds. The stimulating voltage was prescribed such that sinus bradycardia became maximum within the range in which the sinus rhythm did not disappear.

Ten minutes after the occurrence of continuous arrhythmia, the vagus nerve was stimulated, and after it was confirmed that bradycardia did not occur, the test compound was continuously injected into the femoral vein at a rate of 0.5 mg/kg/min. After the administration, the vagus nerve was stimulated every minute, and the inhibition of extrasystole was observed. At the same time, the presence or absence of restoration of the cardiogram to a normal rhythm was observed using the inversion of R waves as an index in ventricular arrhythmia. The anti-arrhythmic action was evaluated such that when the normal sinus rhythm was restored and extrasystole was not induced by stimulation of the vagus nerve, the result was rated as complete inhibition. The dose required for complete inhibition was shown in Table 2.

TABLE 2

| Test compound | Dose (mg/kg) required complete inhibition (mg/kg) (*) |
| --- | --- |
| 28 | 1.5–2.8 |
| 33 | 2.0–3.0 |
| Mexiletine | 2.0–4.5 |

(*) n=3 (range)

The results of the above Test Examples show that the compounds of formula (I) provided by this invention have very strong inhibiting activity on chloroform-induced arrhythmia in mice and ouabain-induced arrhythmia in dogs, and are useful as anti-arrhythmic agents.

Thus, according to this invention, there can be provided a pharmaceutical composition comprising an antiarrhythmically effective amount of the substituted anilide derivative of formula (I) or its pharmaceutically acceptable acid addition salt and a pharmaceutically acceptable diluent or carrier.

The compounds of formula (I) in accordance with this invention can be administered orally or parenterally as anti-arrhythmically active medicaments. Their activity is long-lasting and useful for the treatment and prevention of arrhythmia.

Preferably, the compound of formula (I) or its acid addition salt is used as an antiarrhythmically active medicament in the form of tablets, sublingual tablets, capsules, powders, granules, suppositories, liquids, injecting preparations, suspensions, etc. prepared by using pharmaceutically acceptable diluents or carriers such as vehicles, binders, solvents and emulsifiers.

Examples of the vehicles are starches such as potato starch, wheat starch and corn starch, sugars such as lactose, sucrose, glucose, mannitol and sorbitol, celluloses such as crystalline cellulose, carboxy methyl cellulose calcium and hydroxypropyl cellulose, and inorganic substances such as calcium phosphate, calcium sulfate, calcium carbonate and talc.

Examples of the binders are starch, gelatin, gum arabic, methyl cellulose, carboxy methyl cellulose sodium, polyvinyl pyrrolidone and hydroxypropyl cellulose.

Examples of the emulsifiers are polyhydric alcohol ester-type nonionic surface-active agents and polyoxyethylene-type nonionic surface-active agents, such as fatty acid monoglycerides, sorbitan fatty acid esters, sucrose and polyglycerol fatty acid esters.

The dosage of the pharmaceutical composition of this invention varies depending upon the condition of a patient. Usually, it is 10 to 1,000 mg, preferably 150 to 600 mg, per day as the compound of formula (I) or its pharmaceutically acceptable acid addition salt in the case of oral or intravenous administration.

The acute toxicity of the compounds of formula (I) or the pharmaceutically acceptable acid addition salts thereof in accordance with this invention corresponds to an $LD_{50}$ value of 200 to 400 mg/kg in oral administration to mice, and therefore, they have very low toxicity.

The following examples will illustrate the present invention more specifically.

EXAMPLE 1

3-Amino-5'-methoxy-2'-(2-pyridyl)butynanilide:

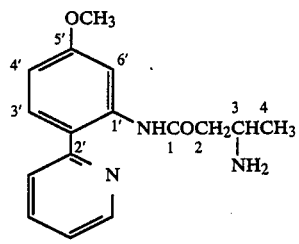

(1) 1.63 g of 2-(4-methoxy-2-nitrophenyl)pyridine was dissolved in 14 ml of ethanol, and 8 g of stannous chloride dihydrate and 5.7 ml of concentrated hydrochloric acid were added. The mixture was stirred at a bath temperature of 100° C. for 3 hours. After cooling, the reaction mixture was made alkaline with a 50% aqueous solution of sodium hydroxide and extracted with benzene. The solvent was evaporated. The resulting dark brown oil was subjected to silica gel column chromatography and the column was eluted with chloroform. As a yellow oil, 967 mg (yield 68.2%) of 2-(2-amino-4-methoxyphenyl)pyridine was obtained.

(2) The resulting compound and a solution of 1.280 g of 3-t-butoxycarbonylaminobutyric acid and 1.21 g of 1-ethyl-3-(3-dimethylaminopropyl)carbodiimide monohydrochloride in 15 ml of methylene chloride were stirred at room temperature for 3 hours. The reaction mixture was washed with water, and the solvent was evaporated. The residue was subjected to silica gel column chromatography, and the column was eluted with chloroform. The eluate was recrystallized from ethyl acetate/hexane to give 1.574 g (yield 84.5%) of 3-t-butoxycarbonylamino-5'-methoxy-2'-(2-pyridyl)-butyranilide as pale yellow prisms having a melting point of 143° to 145° C.

(3) The resulting t-butoxycarbonyl compound (1.50 g) was dissolved in 39 ml of methanol, and 6.5 ml of 6N-hydrochloric acid was added. The solution was stirred at a bath temperature of 80° C. for 1 hour. The solvent was evaporated, and the residue was made alkaline with a dilute aqueous solution of sodium hydroxide and extracted with ethyl acetate. The solvent was evaporated. The resulting reddish brown oil was subjected to silica gel column chromatography, and the column was eluted with a 30:1 mixture of chloroform/methanol (containing ammonia). The solvents were evaporated from the eluate to give 994 mg (yield 89.5%) of 3-amino-5'-methoxy-2'-(2-pyridyl)butyranilide.

NMR(CDCl$_3$) δ: 1.16 (3H, d, J=6 Hz, CH$_3$); 1.77 (2H, br.s, NH$_2$); 2.32 (1H, d,d, J=8, 16 Hz, COCH); 2.52 (1H, d,d J=6, 16 Hz, COCH); 3.34–3.68 (1H, m, CH); 4.87 (3H, s, OCH$_3$); 6.71 (1H, d,d, J=8 Hz, aromatic H); 7.12–7.32 (1H, m, aromatic H); 7.52–7.90 (3H, m, aromatic H); 8.32 (1H, d, J=2 Hz, aromatic H); 8.53–8.67 (1H, m, aromatic H); 12.65 (1H, m, NHCO).

IR $\nu_{max}^{film}$ cm$^{-1}$: 1669

Mass m/e: 285 (M+)

The hydrochloride of the above product is a colorless crystalline powder having a melting point of 185° to 188° C.

EXAMPLES 2-14

The following compounds were prepared by performing the same procedure as described in Example 1.

EXAMPLE 2

3-Amino-5'-methoxy-2'-(3-pyridyl)butyranilide

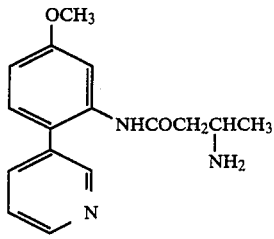

Slightly brown oil
NMR(CDCl₃) δ: 1.10 (3H, d, J=6 Hz, CH₃); 1.32 (2H, m, NH₂); 2.0-2.52 (2H, m, COCH₂); 2.88-3.36 (1H, m, CH); 3.88 (3H, s, OCH₃); 6.78 (1H, d,d, J=3 8 Hz, aromatic H); 7.16 (1H, d, J=8 Hz, aromatic H); 7.30-7.56 (1H, m, aromatic H); 7.64-7.84 (1H, m, aromatic H); 8.06 (1H, d, J=3 Hz, aromatic H), 8.58-8.76 (2H, m, aromatic H).
IR $\nu_{max}^{film}$ cm⁻¹: 3348, 3239, 1671, 1612, 1579, 1529

EXAMPLE 3

3-Amino-5'-chloro-2'-(2-pyridyl)butyranilide monohyirochloride

Slightly yellow powder
Melting point: 220°-222° C. (methanol-ether)
NMR(CD₃OD) δ: 1.39 (3H, d, J=6 Hz, CH₃); 2.79 (2H, d, J=6 Hz, COCH₂); 3.58-3.94 (1H, m, CH); 7.20-7.56 (2H, m, aromatic H); 7.75-8.13 (3H, m, aromatic H); 8.47 (1H, d, J=2 Hz, aromatic H); 8.68-8.84 (1H, m, aromatic H).
IR $\nu_{max}^{Br}$ cm⁻¹: 1684, 1585, 1523, 1422, 769.

EXAMPLE 4

3-Amino-5'-methoxy-2'-(4-pyridyl)butyranilide monohydrochloride

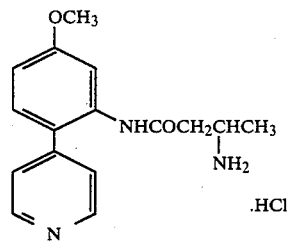

Pale yellow prisms
Melting point: 213°-214° C. (methanol-ether)
NMR (CD₃OD) δ: 1.28 (3H, d, J=7 Hz, CH₃); 2.64 (2H, d, J=7 Hz, COCH₂); 3.5-3.8 (1H, m, CH); 3.87 (3H, s, OCH₃); 6.99 (1H, d,d, J=3.8 Hz, aromatic H); 7.16 (1H, d, J=3 Hz, aromatic H); 7.39 (1H, d, J=8 Hz, aromatic H); 7.4-7.64 (2H, m, aromatic H); 8.44-8.74 (2H, m, aromatic H).
IR $\nu_{max}^{KBr}$ cm⁻¹: 3420, 3244, 2910, 1693, 1605, 1530, 1211, 1040, 843, 811.

EXAMPLE 5

3-Amino-5'-chloro-2'-(3-pyridyl)butyranilide monohydrochloride

Pale yellow powder (hygroscopic)
NMR(CD₃OD) δ: 1.27 (3H, d, J=7 Hz, CH₃); 2.61 (2H, d, J=6 Hz, COCH₂); 3.4-3.7 (1H, m, CH); 7.44 (2H, s. aromatic H); 7.56-7.80 (2H, m, aromatic H); 7.92-8.11 (1H, m, aromatic H); 8.50-8.90 (2H, m, aromatic H).
IR $\nu_{max}^{KBr}$ cm⁻¹: 3392, 2963, 1662, 1521, 1190, 1092, 803, 711.

EXAMPLE 6

3-Amino-2'-(2-pyridyl)-5'-(trifluoromethyl)butyranilide monohydrochloride

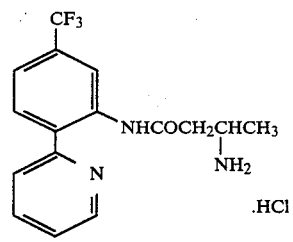

Colorless fine needles
Melting point: 245°-246° C. (methanol-ether)
NMR(CD₃OD) δ: 1.40 (3H, d, J=6 Hz, CH₃); 2.82 (2H, d, J=6 Hz, COCH₂); 3.59-3.95 (1H, m, CH); 7.38-7.72 (2H, m, aromatic H); 7.90-8.18 (3H, m, aromatic H); 8.74-8.92 (2H, m, aromatic H).
IR $\nu_{max}^{KBr}$ cm⁻¹: 3413, 1666, 1591, 1549, 1432, 1332, 1008, 781.

EXAMPLE 7

3-Amino-2'-(3-pyridyl)-5'-(trifluoromethyl)butyranilide

Pale brown oil
NMR (CDCl₃) δ: 1.00 (2H, br.s, NH₂); 1.09 (3H, d, J=6 Hz, CH₃); 2.12 (1H, d,d, J=8, 16 Hz, COCH); 2.38 (1H, d,d, J=4, 16 Hz, COCH); 2.88-3.28 (1H, m, CH); 7.26-7.56 (3H, m, aromatic H); 7.64-7.92 (1H, m, aromatic H); 8.60-8.87 (3H, m, aromatic H); 10.85 (1H, m, NHCO).
IR $\nu_{max}^{film}$ cm⁻¹: 1674, 1581, 1545, 1428, 1330, 1165, 1123.

EXAMPLE 8

3-Amino-5'-methyl-2'-(2-pyridyl)butyranilide

Slightly yellow oil
NMR (CDCl₃) δ: 1.16 (3H, d, J=6 Hz, CH₃); 1.54 (2H, s, NH₂); 2.43 (3H, s, CH₃); 3.32-3.64 (1H, m, CH); 7.02 (1H, d, J=8 Hz, aromatic H); 7.20-7.40 (1H, m, aromatic H); 7.59 (1H, d, J=8 Hz, aromatic H); 7.66-8.00 (2H, m, aromatic H); 8.46 (1H, s, aromatic H); 8.60-8.80 (1H, m, aromatic H); 12.30 (1H, br.s, NHCO).
IR $\nu_{max}^{film}$ cm⁻¹: 1675, 1616, 1579, 1533, 1469, 1422, 782, 744.

EXAMPLE 9

3-Amino-5'-methyl-2'-(3-pyridyl)butyranilide monohydrochloride

Pale yellow powder
NMR (CD₃OD) δ: 1.25 (3H, d, J=6 Hz, CH₃); 2.42 (3H, s, CH₃); 2.59 (2H, d, J=6 Hz, COCH₂); 3.4-3.72

(1H, m, CH); 7.29–7.46 (3H, m, aromatic H); 7.48–7.74 (1H, m, aromatic H); 7.89–8.06 (1H, m, aromatic H); 8.51–8.74 (2H, m, aromatic H).

IR $\nu$ KBr cm: 3400, 3143, 1655, 1526, 806, 712.

EXAMPLE 10

3-Amino-5'-methyl-2'-(4-pyridyl)butyranilide

Pale yellow oil

NMR(CDCl$_3$) $\delta$: 1.10 (3H, d, J=6 Hz, CH$_3$); 1.20 (2H, br.s, NH$_2$); 2.0–2.57 (5H, m, COCH$_2$ and CH$_3$); 3.0–3.38 (1H, m, CH); 6.96–7.26 (2H, m, aromatic H); 7.32–7.50 (2H, m, aromatic H); 8.13 (1H, s, aromatic H); 8.67–8.88 (2H, m, aromatic H); 9.90–10.20 (1H, m, NHCO).

IR $\nu_{max}^{film}$ cm$^{-1}$: 3250, 1660, 1598, 1530, 1501, 809, 749.

EXAMPLE 11

3-Amino-2'-methoxy-6'-(2-pyridyl)butyranilide

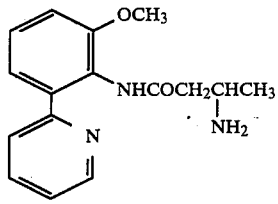

Colorless prisms

Melting point: 125.5°–126.5° C. (ether)

NMR(CDCl$_3$) $\delta$: 1.06 (3H, d, J=6 Hz, CH$_3$); 1.48 (2H, br.s, NH$_2$); 2.01–2.47 (2H, m, COCH$_2$); 3.11–3.42 (1H, m, CH); 3.91 (3H, s, OCH$_3$); 6.95–7.44 (4H, m, aromatic H); 7.48–7.67 (1H, m, aromatic H); 7.67–7.88 (1H, m, aromatic H); 8.56–8.70 (1H, m, aromatic H); 9.08–9.50 (1H, m, NHCO).

IR $\nu_{max}^{KBr}$ cm$^{-1}$: 3395, 3350, 3205, 1671, 1585, 1562, 1522, 1030, 774.

EXAMPLE 12

3-Amino-2'-methoxy-5'-(4-pyridyl)butyranilide monohydrochloride

Colorless prisms

Melting point: 247°–249° C. (decomp.) (methanol-ether)

NMR(CD$_3$OD) $\delta$: 1.46 (3H, d, J=6 Hz, CH$_3$); 2.92 (2H, d, J=6 Hz, COCH$_2$); 4.01 (3H, s, OCH$_3$); 7.23 (1H, d, J=8 Hz, aromatic H); 7.69 (1H, d,d, J=2, 8 Hz, aromatic H); 7.80–8.04 (2H, m, aromatic H); 8.32–9.00 (3H, m, aromatic H and NHCO).

IR $\nu_{max}^{KBr}$ cm$^{-1}$: 3405, 3234, 2913, 1689, 1170, 789.

EXAMPLE 13

3-Amino-2'-methoxy-5'-(3-pyridyl)butyranilide monohydrochloride

Colorless powder

Melting point: 138°–140° C. (methanol-ether)

NMR(CD$_3$OD) $\delta$: 1.44 (3H, d, J=6 Hz, CH$_3$); 2.78–3.00 (2H, m, COCH$_2$); 3.60–4.0 (1H, m, CH); 3.97 (3H, s, OCH$_3$); 7.19 (1H, d, J=8 Hz, aromatic H); 7.42–7.65 (2H, m, aromatic H); 8.01–8.21 (1H, m, aromatic H); 8.36–8.61 (2H, m, aromatic H); 8.74–8.92 (1H, m, aromatic H).

IR $\nu_{max}^{KBr}$ cm$^{-1}$ 3400, 1663, 1540, 1489, 796.

EXAMPLE 14

3-Amino-2'-methoxy-5'-(2-pyridyl)butyranilide monohydrochloride

Colorless needles

Melting point: 174°–176° C. (methanol-ether)

(Free base): NMR(CDCl$_3$) $\delta$: 1.22 (3H, d, J=6 Hz, CH$_3$; 1.66 (2H, br.s, NH$_2$); 2.32 (1H, d,d, J=8, 16 Hz, COCH); 2.54 (1H, d,d, J=4, 16 Hz, COCH); 3.35–3.62 (1H, m, CH); 3.92 (3H, s, OCH ); 7.00 (1H, d, J=8 Hz, aromatic H); 7.10–7.30 (1H, m, aromatic H); 7.70–7.95 (3H, m, aromatic H); 8.63–8.78 (1H, m, aromatic H); 9.03 (1H, d, J=2 Hz, aromatic H); 9.55 (1H, br.s, NHCO).

IR $\nu_{max}^{KBr}$ cm$^{-1}$: 3400, 1662, 1467.

EXAMPLE 15

2-Amino-2'-(5-pyridyl)-5'-(2,2,2-trifluoroethoxy)-propionanilide

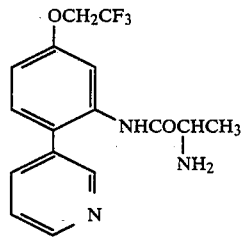

(1) 1.235 g of 3-(4-methoxy-2-nitrophenyl)pyridine was dissolved in 100 ml of a 47% aqueous solution of hydrogen bromide, and the solution was stirred at a bath temperature of 120° C. for 8 hours. After cooling, the reaction mixture was adjusted to pH 3–4 with a 50% aqueous solution of sodium hydroxide, neutralized with sodium hydrogen carbonate, and extracted with ethyl acetate. The solvent was evaporated, and the crude crystals were recrystallized from ethyl acetate to give 477 mg of 3-(4-hydroxy-2-nitrophenyl)pyridine. The recrystallization mother liquor was subjected to silica gel column chromatography, and the column was eluted with a 50:1 mixture of chloroform and ethanol. The solvent was evaporated to give 331 mg of the above compound. The total amount of the above compound was 808 mg (yield 69.7%).

(2) 649 mg of the resulting compound was dissolved in 6 ml of N,N'-dimethylformamide, and 622 mg of potassium carbonate and 1.68 g of 1-(2,2,2-trifluoroethanol) trifluoromethanesulfonate were added and the mixture was stirred at a bath temperature of 50° C. for 1 hour. After cooling, 60 ml of ethyl acetate was added, and the mixture washed with water. Evaporation of the solvent gave a dark brown oil. The oil was subjected to silica gel column chromatography, and the column was eluted with chloroform. The solvent was evaporated from the eluate to give 765 mg (yield 85.5%) of 3-2-nitro-4-(2,2,2-trifluoroethoxy)phenyl]pyridine as a brown oil.

(3) The product was then worked up as in Example 1, (1) to give 680 mg (yield 98.8%) of 3-2-amino-4-(2,2,2-trifluoroethoxy)phenyl)pyridine as reddish brown (4) 330 mg of the resulting compound, 303 mg of N-t-butoxycarbonylalanine, and 307 mg of 1-ethyl-3-(3-dimethylaminopropyl)carbodiimide hydrochloride were dissolved in 5 ml of methylene chloride, and the solution was stirred overnight at room temperature.

The solvent was evaporated, and the resulting oil was subjected to silica gel column chromatography. The column was eluted with chloroform, and the resulting crude crystals were recrystallized from a mixture of ethyl acetate and hexane to give 414 mg (yield 76.2%) of 2-(t-butoxycarbonylamino)-2'-(3-pyridyl)-5'-(2,2,2-trifluoroethoxy)propionanilide as a colorless crystalline powder having a melting point of 149° to 152° C.

(5) 383 mg of the resulting t-butoxycarbonyl compound was dissolved in 4.5 ml of methanol, and 0.75 ml of 6N-hydrochloric acid was added. The solution was stirred at a bath temperature of 70° C., and then worked up in the same way as in Example 1, (3) to give 271 mg (yield 91.6%) of 2-amino-2'-(3-pyridyl)-5'-(2,2,2-trifluoroethoxy)propionanilide as a pale yellow oil.

NMR (CDCl$_3$) δ: 1.34 (3H, d, J=7 Hz, CH$_3$); 1.45 (2H, br.s, NH$_2$); 3.53 (1H, q, J=7 Hz, COCH); 4.45 (2H, q, OCH ); 6.87 (1H, d,d, J=3, 8 Hz, aromatic H); 7.24 (1H, d, J=8 Hz, aromatic H); 7.36–7.60 (1H, m, aromatic H); 7.69–7.87 (1H, m, aromatic H); 8.25 (1H, d, J=3 Hz, aromatic H); 8.63–8.82 (2H, m, aromatic H); 9.88 (1H, br.s, NHCO).

IR ν$_{max}$$^{KBr}$ cm$^{-1}$: 1679.

The hydrochloride of this product is a colorless powder having a melting point of 135° to 140° C.

EXAMPLES 16–25

The following compounds were produced by performing the same procedure as in Example 15.

EXAMPLE 16

2-Amino-2'-(2-pyridyl)-5'-(2,2,2-trifluoroethoxy)propionanilide

Colorless prisms
Melting point: 85°–86° C. (ethyl acetate-hexane)
NMR(CDCl$_3$) δ: 1.45 (3H, d, J=8 Hz, CH$_3$); 1.60 (2H, s, NH$_2$); 3.53–3.84 (1H, m, CH); 4.48 (2H, q, J=8 Hz, OCH ); 6.84 (1H, d,d, J=2, 8 Hz, aromatic H); 7.20–7.44 (1H, m, aromatic H); 7.61–8.04 (3H, m, aromatic H); 8.48 (1H, d, J=2 Hz, aromatic H); 8.62–8.81 (1H, m, aromatic H).

IR ν$_{max}$$^{KBr}$ cm$^{-1}$: 1675, 1607, 1590, 1524, 1471, 1427, 1287, 1156, 978, 844, 781.

EXAMPLE 17

2-Amino-3'-ethoxy-2'-(3-pyridyl)propionanilide monohydrochloride

Pale yellow granular crystals
Melting point: 207°–209° C. (ethyl acetate-hexane)
NMR(CDCl$_3$-CD$_3$OD) δ: 1.40 (3H, d, J=6 Hz, CH$_3$); 1.42 (3H, t, J=8 Hz, OCH$_2$CH$_3$); 4.05 (2H, q, J=8 Hz, OCH ); 4.17 (1H, q, J=6 Hz, CH); 6.89 (1H, d, J=9 Hz, aromatic H); 7.13 (1H, d, J=2 Hz, aromatic H); 7.23 (1H, d, J=9 Hz, aromatic H); 7.44 (1H, m, aromatic H); 7.83 (1H, d, J=8 Hz, aromatic H); 8.55 (2H, m, aromatic H).

IR ν$_{max}$$^{KBr}$ cm$^{-1}$: 3417, 1671, 1611.

EXAMPLE 18

2-Amino-5'-(2-pyridyl)-2'-(2,2,2-trifluoroethoxy)propionanilide monochloride

Colorless powder
Melting point: 136°–140° C. (methanol-ether)
NMR(CD OD) δ: 1.66 (3H, d, J=7 Hz, CH$_3$); 4.30 (1H, q, J=7 Hz, CH); 4.74 (2H, q, J=8 Hz, OCH$_2$CF$_3$); 7.23–7.49 (2H, m, aromatic H); 7.75–8.05 (3H, m, aromatic H); 8.43 (1H, d, J=2 Hz, aromatic H); 8.57–8.79 (1H, m, aromatic H).

IR ν$_{max}$$^{KBr}$ cm$^{-1}$: 3407, 1684, 1258, 1158, 778.

EXAMPLE 19

3-Amino-2'-(2-pyridyl)-5'-(2,2,2-trifluoroethoxy)butyranilide

Slightly brown prisms Melting point: 66°–68° C. (ether-petroleum ether)
NMR(CDCl$_3$) δ: 1.17 (3H, d, J=6 Hz, CH$_3$); 1.69 (2H, s, NH$_2$); 2.35 (1H, d,d, J=8, 15 Hz, COCH); 2.55 (1H, d,d, J=5'15 Hz, COCH); 3.32–3.76 (1H, m, CH); 4.47 (2H, q, J=8 Hz, OCH ); 6.79 (1H, d,d, J=2, 8 Hz, aromatic H); 7.20–7.44 (1H, m, aromatic H); 7.60–7.99 (3H, m, aromatic H); 8.44 (1H, d, J=2 Hz, aromatic H); 8.60–8.80 (1H, m, aromatic H).

IR ν$_{max}$$^{KBr}$ cm$^{-1}$: 1680, 1615, 1590, 1472, 1430, 1210, 1156, 1080, 779.

The monohydride of this compound is in the form of colorless needles having a melting point of 184° to 186° C. (acetone-ether).

EXAMPLE 20

3-Amino-2'-(3-pyridyl)-5'-(2,2,2-trifluoroethoxy)butyranilide monohydrochloride

Colorless crystalline powder
Melting point: 218°–219° C. (methanol-ether)
NMR(CDCl$_3$) δ: 1.27 (3H, d, CH$_3$); 2.61 (2H, d, J=6 Hz, COCH$_2$); 3.44–3.74 (1H, m, CH); 4.61 (2H, d, J=8 Hz, OCH$_2$CF$_3$); 7.09 (1H, d,d, J=3, 8 Hz, aromatic H); 7.30 (1H, d, J=3 Hz, aromatic H); 7.40 (1H, d, J=8 Hz, aromatic H); 7.44–7.74 (1H, m, aromatic H); 7.83–8.08 (1H, m, aromatic H); 8.4–8.8 (2H, m, aromatic H).

IR ν$_{max}$$^{KBr}$ cm$^{-1}$: 3400, 3180, 2527, 1679, 1613, 1526, 1160, 975, 811.

EXAMPLE 21

3-Amino-2'-(4-pyridyl)-5'-(2,2,2-trifluoroethoxy)butyranilide monohydrochloride

Pale yellow prisms
Melting point: 228°–232° C. (methanol-ether)
NMR(CD$_3$OD) δ: 1.28 (3H, d, J=7 Hz, CH$_3$); 2.63 (2H, d, J=6 Hz, COCH ); 3.48–3.76 (1H, m, CH); 4.62 (2H, q, J=8 Hz, OCH ); 7.10 (1H, d,d, J=3, 8 Hz, aromatic H); 7.30 (1H, d, J=3 Hz, aromatic H); 7.36 (1H, d, J=8 Hz, aromatic H); 7.46–7.64 (2H, m, aromatic H); 8.48–8.80 (2H, m, aromatic H).

IR ν$_{max}$$^{KBr}$ cm$^{-1}$: 3410, 3182, 1687, 1610, 1176, 1162, 813.

EXAMPLE 22

3-Amino-2'-(2-pyridyl)-6'-(2,2,2-trifluoroethoxy)butyranilide

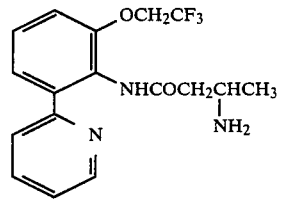

Colorless slightly needle-like crystals
Melting point: 135°–137° C. (ethyl acetate-hexane)

NMR(CDCl₃) δ: 1.11 (3H, d, J=6 Hz, CH₃); 1.41 (2H, br.s, NH); 2.09-2.48 (2H, m, COCH₂); 3.14-3.52 (1H, m, CH); 4.48 (2H, q, J=8 Hz, OCH₂CF); 6.92-7.20 (2H, m, aromatic H); 7.55-7.96 (2H, m, aromatic H); 8.62-8.76 (1H, m, aromatic H); 9.70-10.08 (1H, m, NHCO).

IR $\nu_{max}^{KBr}$ cm⁻¹: 3424, 3355, 1670, 1257, 1174, 1155, 988, 978, 774.

EXAMPLE 23

3-Amino-2'-(3-pyridyl)-6'-(2,2,2-trifluoroethoxy)-butyranilide

Colorless crystalline powder
Melting point: 165°-168° C.
NMR(CD₃OD) δ: 1.02 (3H, d, J=6 Hz, CH₃); 2.25 (2H, d, J=6 Hz, COCH₂); 3.1-3.4 (1H, m, CH); 4.62 (2H, q, J=8 Hz, OCH₂CF₃); 7.10-7.38 (2H, m, aromatic H); 7.42-7.66 (2H, m, aromatic H); 7 82-8.0 (1H, m, aromatic H); 8.54-8.72 (2H, m, aromatic H).

IR $\nu_{max}^{KBr}$ cm⁻¹: 3421, 1663, 1550, 1457, 1260, 1155, 782, 714.

EXAMPLE 24

3-Amino-5'-(2-pyridyl)-2'-(2,2,2-trifluoroethoxy)-butyranilide monohydrochloride Colorless crystalline powder
Melting point: 202°-207° C. (methanol-ether)
NMR(CD₃OD) δ: 1.44 (3H, d, J=7 Hz, CH₃); 2.87 (2H, d, J=6 Hz, COCH₂); 3.56-3.94 (1H, m, CH); 4.73 (2H, q, J=8 Hz, OCH ; 7.20-7.53 (2H, m, aromatic H); 7.72-8.12 (3H, m, aromatic H); 8.50 (1H, d, J=2 Hz, aromatic H); 8.57-8.74 (1H, m, aromatic H).

IR$_{max}^{KBr}$ cm−1: 3411, 3290, 1662, 1541, 1257, 1156, 777.

EXAMPLE 25

3-Amino-5'-(4-pyridyl)-2'-(2,2,2-trifluoroethoxy)-butyranilide monohydrochloride Colorless fine needles
Melting point: 210°-212° C. (methanol-ether)
NMR(CD₃OD) δ: 1.45 (3H, d, J=6 Hz, CH₃); 2.88 (2H, d, J=6 Hz, COCH₂); 3.6-4.0 (1H, m, CH); 4.74 (2H, q, J=8 Hz, OCH ); 7.32 (1H, d, J=8 Hz, aromatic H); 7.60-7.84 (3H, m, aromatic H); 8.36 (1H, d, J=3 Hz, aromatic H); 8.56-8.80 (2H, m, aromatic H).

IR $\nu_{max}^{KBr}$ cm⁻¹: 3420, 3268, 1688, 1600, 1547, 1484, 1147, 960, 802.

EXAMPLE 26

2-(3,4-Dimethoxyphenethylamino)-5'-methoxy-2'-(2-pyridyl)acetanilide

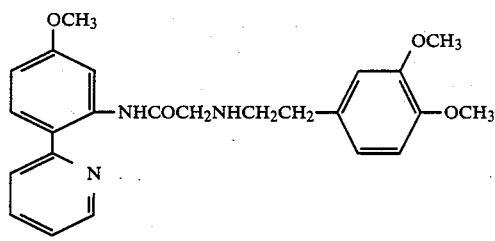

(1) 351 mg of N-(3,4-dimethoxyphenethyl)-N-(trifluoroacetyl)glycine was dissolved in 5 ml of benzene, and one drop of pyridine and 147 mg of oxalyl chloride were added. The mixture was heated under reflux for 1 hour. The solvent was evaporated, and the residue was dissolved in 3 ml of tetrahydrofuran. Under ice cooling, mg of 2-(2-amino-4-methoxyphenyl)pyridine and 106 ml of triethylamine were added. The mixture was stirred overnight at room temperature. The solvent was evaporated, and an aqueous solution of sodium hydrogen carbonate was added. The mixture was extracted with ethyl acetate. The solvent was evaporated, and the residue was subjected to silica gel column chromatography. The column was eluted with chloroform, and the solvent was evaporated to give 252 mg (yield 55.8%) of 2-[(3,4-dimethoxyphenethyl)trifluoroacetyl]amino)-5'-methoxy-2'-(2-pyridyl)acetanilide.

(2) The resulting compound was dissolved in 40 ml of ammonia-saturated methanol, and in a sealed tube, the solution was heated at a bath temperature of 80° C. for hours. The solvent was evaporated, and the residue was subjected to silica gel column chromatography. The column was eluted with a 100:1 mixture of chloroform and methanol (containing ammonia), and the solvent was evaporated from the eluate. There was obtained 194 mg (yield 94.6%) of 2-(3,4-dimethoxyphenethylamino)-5'-methoxy-2'-(2-pyridyl)acetanilide as an oil.

NMR(CDCl₃) δ: 2.60-3.00 (4H, m, NHCH₂CH₂); 3.45 (2H, s, COCH₂N); 3.85 (6H, s, OCH₃); 3.90 (3H, s, OCH₃); 6.70-8.45 (10H, m, aromatic H).

IR $\nu_{max}^{CHCl3}$ cm⁻¹: 1663

EXAMPLES 27-39

The following compounds were produced by performing the same procedure as in Example 1, 15 or 26.

EXAMPLE 27

3-Amino-5'-methoxy-2'-(2-pyridyl)-3-(3,4,5-trimethoxyphenyl)propionanilide

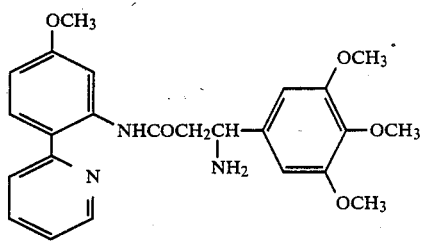

Oil
NMR(CDCl₃) δ: 2.65-2.80 (2H, m, COCH₂); 3.85-3.90 (12H, m, OCH₃); 6.70 (2H, s. aromatic H); 6.80-8.60 (7H, m, aromatic H)
IR $\nu_{max}^{CHCl3}$ cm⁻¹: 1670, 1125
Mass m/e: 437 (M⁺)

EXAMPLE 28

5'-Allyloxy-3-amino-2'-(3-pyridyl)butyranilide

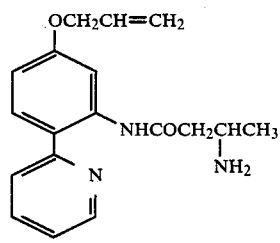

Pale yellow oil

NMR(CDCl$_3$) δ: 1.08 (3H, d, J=6 Hz, CH$_3$); 4.65 (2H, d, J=6 Hz, OCH$_2$); 5.33-5.60 (2H, m, CH=CH$_2$); 6.00-6.40 (1H, m, —OCH$_2$CH=CH$_2$); 6.83-8.75 (7H, m, aromatic H).

IR $\nu_{max}^{CHCl_3}$ cm$^{-1}$: 1668, 1650

Mass m/e: 311 (M$^+$)

EXAMPLE 29

3-Amino-5'-propoxy-2'-(3-pyridyl)butyranilide

Colorless oil

NMR(CDCl$_3$) δ: 1.05 (3H, t, J=7 Hz, —OCH$_2$CH$_3$); 1.08 (3H, d, J=7 Hz, CHCH$_3$); 1.36 (2H, s, NH$_2$); 1.67-2.00 (2H, m, —OCH$_2$CH$_2$); 2.12 (1H, d,d, J=4,17 Hz, COCH); 2.38 (1H, d,d, J=4,17 Hz, COCH); 3.16 (1H, m, CH); 4.00 (2H, t, J=8 Hz, OCH$_2$); 6.77 (1H, m, aromatic H); 7.72 (1H, d, J=8 Hz, aromatic H); 8.03 (1H, d, J=3 Hz, aromatic H); 8.57-8.70 (2H, m, aromatic H).

IR $\nu_{max}^{film}$ cm$^{-1}$: 1667, 1611, 1577, 1532.

EXAMPLE 30

2'-Allyloxy-3-amino-5'-(2-pyridyl)butyranilide dihydrochloride

Slightly yellow powder

Melting point: 180°-210° C. (decomp.)

NMR(C$_2$O) δ: 1.55 (3H, d, J=6 Hz, CH$_3$); 3.03 (2H, d, J=6 Hz, COCH$_2$); 5.45-5.75 (2H, m, CH=CH$_2$); 6.00-6.45 (1H, m, -OCH$_2$CH=CH$_2$); 7.40-8.85 (7H, m, aromatic H).

IR $\nu_{max}^{KBr}$ cm$^{-1}$: 1666.

EXAMPLE 31

Ethyl 2-(3-aminobutyramide)-4-(2-pyridyl)phenoxyacetate dihydrochloride

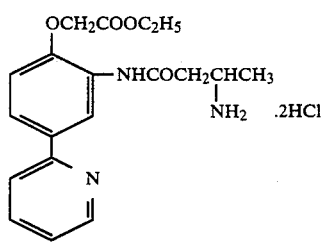

Colorless powder

Melting point: 150°-170° C. (decomp.)

NMR(C$_2$O) δ: 1.38 (3H, t, J=6 Hz, COOC ); 1.55 (3H, d, J=6 Hz, CH$_3$); 3.02 (2H, d, J=6 Hz, COCH$_2$); 4.40 (2H, q, J=6 Hz, COOCH ); 5.05 (2H, s, OCH$_2$COO); 7.35-8.85 (7H, s, aromatic H).

IR $\nu_{max}^{KBr}$ cm$^{-1}$: 1733, 1669.

EXAMPLE 32

3-Amino-5'-isopropoxy-2'-(3-pyridyl)butyranilide

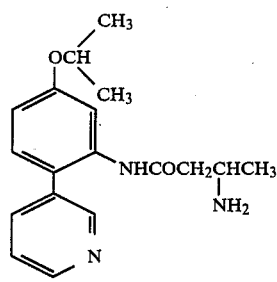

Pale yellow oil

NMR(CDCl$_3$) δ: 1.08 (3H, d, J=6 Hz, CH$_3$); 1.37 (6H, 3, J=6 Hz, CH(CH$_3$)$_2$); 2.16 (1H, d,d, J=9.15 Hz, COCH); 2.40 (1H, d,d, J=4.15 Hz, COCH); 3.16 (1H, m, CH); 4.66 (1H, m, OCH); 6.73 (1H, d,d, J=3.8 Hz, aromatic H); 7.15 (1H, d, J=8 Hz, aromatic H); 7.38 (1H, m, aromatic H); 7.75 (1H, m, aromatic H); 8.04 (1H, d, J=3 Hz, aromatic H); 8.63-8.73 (2H, m, aromatic H).

IR $\nu_{max}^{film}$ cm$^{-1}$: 3239, 2962, 1664, 1609.

EXAMPLE 33

3-Amino-5'-ethoxy-2'-(3-pyridyl)butyranilide dihydrochloride

Colorless needles

Melting point: 229°-230° C. (decomp.)

NMR(C$_2$O) δ: 1.27 (3H, d, J=8 Hz, CH$_3$); 1.46 (3H, t, J=7 Hz, —OCH$_2$CH$_3$); 2.75 (2H, d, J=7 Hz, COCH$_2$); 3.70 (1H, m CH); 4.26 (2H, q, J=7 Hz, OCH$_2$); 7.18 (1H, d, J=2 Hz, aromatic H); 7.23 (1H, d,d, J=2,8 Hz, aromatic H); 7.62 (1H, d, J=8 Hz, aromatic H); 8.25 (1H, d,d, J=5,8 Hz, aromatic H); 8.75 (1H, m, aromatic H); 8.88-8.95 (2H, m, aromatic H).

IR $\nu_{max}^{KBr}$ cm$^{-1}$: 3358, 3198, 2966, 1671, 1602, 1501.

EXAMPLE 34

3-Amino-5'-ethoxy-2'-(2-pyridyl)butyranilide

Yellow oil

NMR(CDCl$_3$) δ: 1.18 (3H, d, J=6 Hz, CH$_3$); 1.43 (3H, t, J=6 Hz, OCH ); 4.17 (2H, q, J=6 Hz, OCH$_2$CH$_3$); 6.77-8.67 (7H, m, aromatic H).

IR $\nu_{max}^{CHCl_3}$ cm$^{-1}$: 1670.

Mass m/e: 299 (M$^+$)

EXAMPLE 35

3-Amino-5'-ethoxy-2'-(4-pyridyl)butyranilide

Pale yellow oil

NMR(CDCl$_3$) δ: 1.10 (3H, d, J=6 Hz, CH$_3$); 1.43 (3H, t, J=7 Hz, OCH$_2$CH$_3$); 4.12 (2H, q, J=6 Hz, OCH$_2$); 6.80-8.70 (7H, m, aromatic H); 7.38 (1H, m, aromatic H); 7.72 (1H, d, J=8 Hz, aromatic H); 8.03 (1H, d, aromatic H); 8.57-8.70 (2H, m, aromatic H).

IR $\nu_{max}^{CHCl_3}$ cm$^{-1}$: 1668.

Mass m/e: 299 (M$^+$)

EXAMPLE 36

3-Amino-2'-(1-imidazolyl)-5'-methoxybutyranilide monohydrochloride

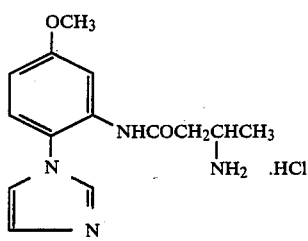

Colorless powder
Melting point: 191°–192° C. (methanol-ether)
NMR(C$_2$O) δ: 1.30 (3H, d, J=6 Hz, CH$_3$); 2.73 (2H, d, J=6 Hz, COCH$_2$); 3.90 (3H, s, OCH$_3$); 7.05–7.83 (6H, m, aromatic H).
IR $\nu_{max}^{KBr}$ cm$^{-1}$: 3396, 1681.

EXAMPLE 37

3-Amino-5'-methoxy-2'-(2-methylsulfinyl-1-imidazolyl)butyranilide

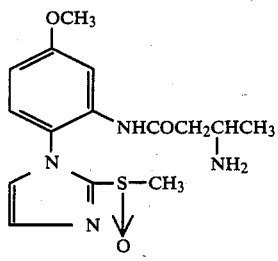

Slightly yellow prisms
Melting point: 177°–178° C.
NMR(CDCl$_3$) δ: 1.05 (3H, d, J=6 Hz, CH$_3$); 3.03 (3H, s, —SOCH$_3$); 3.87 (3H, s, OCH$_3$); 6.65–8.15 (5H, m, aromatic H).
IR $\nu_{max}^{KBr}$ cm$^{-1}$: 1662, 1048.

EXAMPLE 38

3-Amino-5'-methoxy-2'-(2-methylthio-1-imidazolyl)-butyranilide

Pale yellow prisms
Melting point: 149°–150° C.
NMR(CDCl$_3$) δ: 1.10 (3H, d, J=6 Hz, CH$_3$); 2.53 (3H, s, SCH$_3$); 3.87 (3H, s, OCH$_3$); 6.65–8.18 (5H, m, aromatic H).
IR $\nu_{max}^{KBr}$ cm$^{-1}$: 1666.

EXAMPLE 39

N-[5-methoxy-2-(3-pyridyl)phenyl]-N'-phenylurea

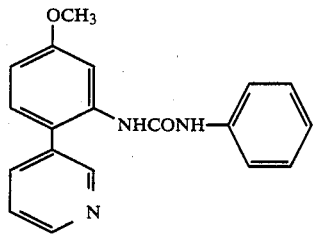

Colorless prisms
Melting point: 166°–167° C.
NMR(DMSO-d$_6$) δ; 3.37 (1H, s, NHCO); 3.83 (3H, s, OCH$_3$); 6.65–8.02 (10H, m, aromatic H); 8.55–8.85 (2H, m, aromatic H); 9.04 (1H, s, NHCO).
IR $\nu_{max}^{KBr}$ cm$^{-1}$: 3340, 1718, 1584, 1529, 1198.

EXAMPLE 40

3-[2-(3-Aminobutyramide)-4-methylphenyl]pyridine N-oxide

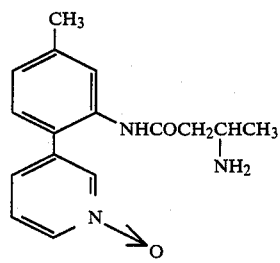

(1) 449 mg of 3-(t-butoxycarbonylamino)-5'-methyl-2'-(3-pyridyl)butyranilide was dissolved in 9 ml of chloroform, and with stirring at room temperature, 395 mg of 80% perbenzoic acid was added. The solution was stirred overnight. The reaction solution was subjected to silica gel column chromatography. The column was eluted with a 30:1 mixture of chloroform and methanol, and the solvent was evaporated from the eluate to give a colorless powder. Recrystallization from ethyl acetate/hexane gave 310 mg (yield 66.2%) of 3-[2-(3-t-butoxycarbonylamino)butyramide-4-methylphenyl]pyridine N-oxide as a colorless powder having a melting point of 172°–173° C.

(2) 270 mg of the resulting t-butoxycarbonyl compound was dissolved in 2.1 ml of methanol and 0.35 ml of N hydrochloric acid was added. The mixture was stirred at a bath temperature of 70° C. for 1 hour. The reaction solution was made alkaline with a 50% aqueous solution of sodium hydroxide, and extracted with ethyl acetate. The extract was washed with a saturated aqueous solution of sodium chloride, and the solvent was evaporated. The resulting oil was subjected to preparative silica gel thin-layer chromatography, and developed with a 10:1 mixed solvent of chloroform and methanol (containing ammonia). The solvent was evaporated to give 179 mg (yield 89.5%) of 3-[2-(3-aminobutyramide)-4-methylphenyl]pyridine N-oxide as a slightly yellow oil.

NMR(CDCl$_3$) δ: 1.16 (3H, d, J=6 Hz, CH$_3$); 1.54 (2H, br.s, NH$_2$); 2.23–2.60 (5H, m, CH$_3$, COCH$_2$); 3.00–3.40 (1H, m, CH); 7.00–7.28 (2H, m, aromatic H); 8.00–8.46 (3H, m, aromatic H).
IR $\nu_{max}^{film}$ cm$^{-1}$: 3333, 3240, 1665, 1571, 1545, 1159, 1015, 891, 749.

EXAMPLE 41

By the same procedure as in Example 40, 4-[3-(3-aminobutyramide)-4-methoxyphenyl]pyridine N-oxide monohydrochloride was produced.
Pale yellow prisms
Melting point: 244°–246° C. (decomp.) (ethyl acetate-methanol)
NMR(CD$_3$OD) δ: 1.46 (3H, d, J=6 Hz, CH$_3$); 2.91 (2H, d, (J=6 Hz, COCH$_2$); 3.56–3.92 (1H, m, CH); 4.00 (3H, s, OCH$_3$); 7.22 (1H, d, J=8 Hz, aromatic H); 63

(1H, d,d, J=2, 8 Hz, aromatic H); 7.78-8.00 (2H, m, aromatic H); 8.32-8.58 (3H, m, aromatic H).

IR $\nu_{max}^{KBr}$ cm$^{-1}$: 3383, 3234, 2917, 1677, 1605, 1403, 1224, 1185, 1020, 837, 798.

EXAMPLE 42

3-(Di-n-butylamino)-5'-methoxy-2'-(2-pyridyl)propionanilide hydrochloride

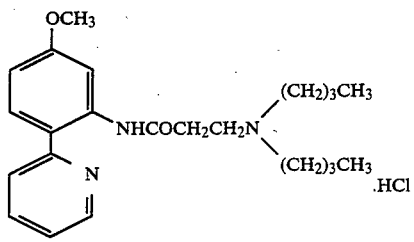

(1) 200 mg of 2-(2-amino-4-methoxyphenyl)pyridine produced in Example 1, (1) was dissolved in 5 ml of tetrahydrofuran, and with stirring under ice cooling, 110 mg of triethylamine and 190 mg of 3-bromopropionyl chloride were added. The mixture was stirred at room temperature for 15 minutes. The solvent was evaporated, and the residue was dissolved in ethyl acetate and washed successively with a saturated aqueous solution of sodium hydrogen carbonate and a saturated aqueous solution of sodium chloride. The solvent was evaporated, and the residue was dissolved in 5 ml of ethanol. 517 mg of di-n-butylamine was added, and the mixture was heated under reflux for 1 hour. The solvent was evaporated, and the residue was subjected to preparative silica gel thin-layer chromatography, and eluted with a 10:1 mixture of chloroform and methanol. The resulting crystals were converted into a hydrochloride in a customary manner. Recrystallization from methanol-ether yielded 200 mg (yield 47.6%) of 3-(di-n-butylamine)-5'-methoxy-2'-(2-pyridyl)propionanilide hydrochloride as a pale pink powder having a melting point of 142° to 144° C.

NMR(C$_2$O) δ: 0.90-2.00 (14H, m, N(CH$_2$CH$_2$CH$_2$CH$_3$)$_2$); 3.93 (3H, s, OCH ); 6.80-8.95 (7H, m, aromatic H).

IR $\nu_{max}^{KBr}$ cm$^{-1}$: 1679.

EXAMPLES 43-46

The following compounds were produced by performing the same procedure as in Example 42.

EXAMPLE 43

5'-Methoxy-3-piperidino-2'-(2-pyridyl)butyranilide

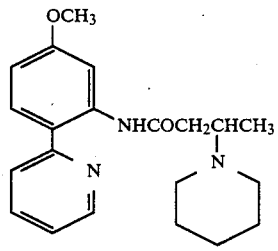

Oil
NMR(CDCl$_3$) δ: 1.08 (3H, d, J=6 Hz, CH$_3$); 1.20-1.80

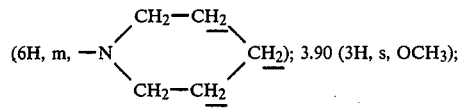 3.90 (3H, s, OCH$_3$);

6.76-8.63 (7H, m, aromatic H).
IR $\nu_{max}^{KBr}$ cm$^{-1}$: 1674.

EXAMPLE 44

3-Dimethylamino-2,-(2-imidazolyl)-5'-methoxypropionanilide hydrochloride

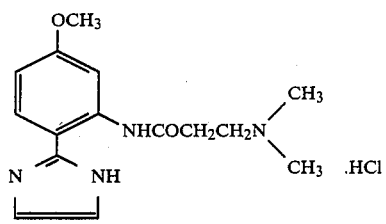

Pale brown needles
Melting point: 189°-190° C. (decomp.)
NMR(CD$_3$OD) δ: 2.96 (6H, s, N(CH$_3$)$_2$); 3.04 (2H, t, J=6 Hz, COCH$_2$CH$_2$N); 3.54 (2H, t, J=6 Hz, COCH$_2$CH$_2$N); 3.87 (3H, s, OCH$_3$); 6.81 (1H, d,d, J=3,9 Hz, aromatic H); 7.20 (2H, s, aromatic H); 7.75 (1H, d, J=9 Hz, aromatic H); 7.65 (1H, d, J=3 Hz, aromatic H).

IR $\nu_{max}^{KBr}$ cm$^{-1}$: 3164, 1681, 1627, 1595, 1426, 1296, 972.

EXAMPLE 45

3-Amino-2'-(2-imidazolyl)-5'-methoxybutyranilide

Brown oil
NMR(CDCl$_3$) δ: 1.10 (3H, d, J=6 Hz, CH$_3$); 2.58 (2H, d, J=6 Hz, COCH$_2$); 3.77 (3H, s, OCH$_3$); 6.56 (1H, d,d, J=2, 8 Hz, aromatic H); 7.05 (2H, s, aromatic H); 7.55 (1H, d, J=8 Hz, aromatic H); 8.35 (1H, d, J=2 Hz, aromatic H).

IR $\nu_{max}^{CHCl_3}$ cm$^{-1}$: 3600-3100, 1673.
Mass m/e: 274 (M$^+$)

EXAMPLE 46

Amino-2'-[2-(1H-imidazo(4,5,b)pyridyl]-5'-methoxybutyranilide

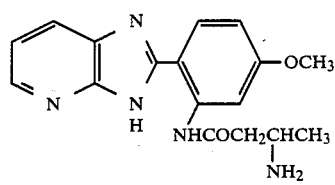

Pale yellow powder
Melting point: 205°-207° C. (chloroform-ether)
NMR(CDCl$_3$) δ: 1.25 (3H, d, J=6 Hz, CH$_3$); 3.85 (3H, s, OCH$_3$); 6.65-8.60 (6H, m, aromatic H).
IR $\nu_{max}^{KBr}$ cm$^{-1}$: 1682.
Mass m/e: 325 (M$^+$)

EXAMPLE 47

N-(2-nitroxyethyl)-5-[3-(3-aminobutyramide)-4-methoxyphenyl]nicotinamide dihydrochloride

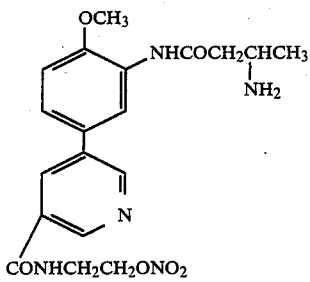

(1) 13.09 g of 4-Bromoanisole was dissolved in 50 ml of tetrahydrofuran, and the solution was cooled to −78° C. with a dry ice-acetone freezing mixture, and 48 ml of m-butyllithium (as a 1.6 M hexane solution). The mixture was stirred for 10 minutes. A tetrahydrofuran solution of 32 ml of triisopropyl borate was added dropwise under cooling over the course of 30 minutes. The temperature of the solution was returned to room temperature, and it was stirred for 10 minutes. Ether was added to the reaction solution, and it was washed with a 10% aqueous solution of hydrochloric acid and water in this order. The solvent was evaporated, and the resulting solid was recrystallized from ether-hexane to give 7.18 g (yield 67.5%) of (4-methoxyphenyl)boric acid as colorless needles having a melting point of 157° to 159° C.

(2) 2.16 g of methyl 5-bromonicotinate and 350 mg of tetrakis(triphenylphosphine)palladium were dissolved in 20 ml of toluene, and under a nitrogen current, 10 ml of a 2M aqueous solution of sodium carbonate and a suspension of 1.82 g of (4-methoxyphenyl)boric acid in 5 ml of methanol were added. The mixture was stirred at a bath temperature of 80° C. for 12 hours. To the reaction solution were added 100 ml of methylene chloride, 50 ml of a 2M aqueous solution of sodium carbonate and 5 ml of conc. aqueous ammonia to perform extraction. The organic layer was separated, and the solvent was evaporated. The residue was subjected to silica gel column chromatography. The column was eluted with a 3:7 mixture of ethyl acetate and hexane. The solvent was evaporated from the eluate to give 600 mg (yield 24.7%) of methyl 5-(4-methoxyphenyl)nicotinate as colorless needles having a melting point of 99° to 101° C.

(3) 1.1 g of the resulting compound was dissolved in 11 ml of 70% nitric acid, and the solution was stirred at room temperature for 20 hours. The reaction mixture was poured into ice water, made alkaline with concentrated aqueous ammonia, and stirred for 30 minutes under ice water cooling. The precipitate was collected by filtration and dissolved in chloroform. The solvent was evaporated, and the resulting crude crystals were recrystallized from methanol-ethyl acetate to give 1.008 g (yield 77%) of methyl 5-(4-methoxy-3-nitrophenyl)-nicotinate as yellow needles having a melting point of 192° to 194° C.

990 mg of the resulting nitro compound was dissolved in 60 ml of ethyl acetate, and 0.3 g of 10% palladium-carbon was added. The nitro compounds was thus catalytically reduced with stirring at 50° C. The catalyst was removed in a customary manner, and the resulting yellow crystals were recrystallized from methylene chloride-ether to give 723 mg (yield 81%) of methyl 5-(3-amino-4-methoxyphenyl)nicotinate as pale yellow needles having a melting point of 98° to 99° C.

(4) 387 mg of the resulting compound and 609 mg of 3-(t-butoxycarbonylamino)butyric acid were treated in the same way as in Example 1, (2) to give 266 mg (yield 40%) of methyl 5-[3-((3-t-butoxycarbonylamino)-butyramide)-4-methoxyphenyl)nicotinate as colorless needles having a melting point of 175° to 177° C.

427 mg of the resulting compound was dissolved in 5 ml of tetrahydrofuran, and a solution of 112 mg of potassium hydroxide in 5 ml of methanol and 0.5 ml of water was added. The solution was stirred at room temperature for 5 hours. The solvent was evaporated. The residue was dissolved in 10 ml of water, and 3 ml of Dowex 50 (H form) as an ion-exchange resin was added. The mixture was stirred and filled in a column. The column was washed with 100 ml of deionized water and then eluted with 5% aqueous ammonia. The eluate was dried under reduced pressure to give 428 mg of a white solid. 258 mg of the white solid was suspended in 10 ml of tetrahydrofuran, and 0.21 ml of triethylamine was added. After cooling with ice water, 253 mg of 2-nitroxyethylamine nitrate was added. Then, 173 mg of 1-ethyl-3-(3-dimethylaminopropyl)carbonyldiimide hydrochloride was added little by little. After 1 hour, 173 mg of the same compound was additionally supplied. The mixture was then stirred for 2 hours.

The solvent was evaporated. Chloroform was added to the residue, and the mixture was washed with water and a saturated aqueous solution of sodium chloride. The solvent was evaporated. The residue was purified by preparative silica gel thin-layer chromatography (developing solvent: chloroform/methanol=9/1) and recrystallized from ethanol-ether to give 63 mg (yield 26.7%) of N-(2-nitroxyethyl)-5-[3-(3-t-butoxycarbonylamino)butyramide-4-methoxyphenyl]nicotinamide as pale yellow needles having a melting point of 108° to 110° C.

(5) 140 mg of the resulting t-butoxycarbonyl compound was dissolved in a mixture of 1.5 ml of tetrahydrofuran and 1.5 ml of methanol. 0.45 ml of a 6N-hydrochloric acid/dioxane solution was added to the solution, and the solution was stirred at a bath temperature of 50° C. for 25 minutes. The precipitated crystals were washed with ether, and dried at 40° C. under reduced pressure to give 91 mg (yield 68%) of N-(2-nitroxyethyl)-5-[3-(3-aminobutyramide)-4-methoxyphenyl]-nicotinamide dihydrochloride as a pale yellow crystalline powder having a melting point of 247° C. (decomp.).

NMR(CD$_3$OD) δ: 1.45 (3H, d, J=7 Hz, CH$_3$); 2.83–3.15 (2H, m, COCH$_2$); 3.1–3.95 (3H, m, CH, NHCH$_2$); 4.04 (3H, s, OCH$_3$); 4.76 (2H, m, CH$_2$ONO$_2$); 7.35 (1H, d, J=9 Hz, aromatic H); 7.79 (1H, d,d, J=2.9 Hz, aromatic H); 8.63–8.75 (2H, m, aromatic H); 9.07–9.51 (2H, m, aromatic H).

IR $\nu_{max}^{KBr}$ cm$^{-1}$: 3408, 3266, 3014, 2900, 1673, 1631.

EXAMPLE 48–51

The following compounds were produced by performing the same procedure as in Example 47.

EXAMPLE 48

Methyl 5-[3-(3-aminobutyramide)phenyl]nicotinate dihydrochloride

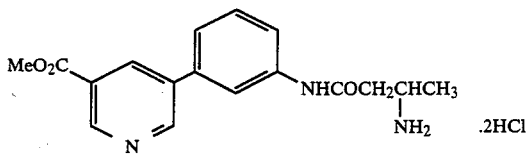

Colorless needles
Melting point: 219°–222° C. (ethanol/ether)
NMR(CD$_3$OD) δ: 1.44 (3H, d, J=7 Hz, CH$_3$); 2.84 (2H, d, J=6 Hz, COCH$_3$); 3.65–3.93 (1H, m, CH); 4.03 (3H, s, COOCH ); 7.44–7.80 (4H, m, aromatic H); 8.06–8.20 (1H, m, aromatic H); 8.64–8.80 (1H, m, aromatic H); 8.98–9.36 (1H, m, aromatic H).
IR $\nu_{max}^{KBr}$ cm$^{-1}$: 3411, 3242, 1732, 1678.

EXAMPLE 49

Methyl 5-[3-(3-aminobutyramide)-4-methoxyphenyl]nicotinate monochloride

Colorless crystalline powder
Melting point: 245°–247° C. (ethanol-ether)
NMR(D$_{20}$) δ: 1.41 (3H, d, J=7 Hz, CH$_3$); 2.81 (2H, d, J=7 Hz, COCH$_2$); 3.24–3.48 (1H, m, CH); 3.78 (3H, s, OCH ); 3.85 (3H, s, COOCH$_3$); 6.68–7.04 (2H, m, aromatic H); 7.60–7.85 (2H, m, aromatic H); 8.32–8.68 (2H, m, aromatic H).
IR $\nu_{max}^{KBr}$ cm$^{-1}$: 3400, 3290, 1730, 1670.

EXAMPLE 50

N-hexyl-5-[2-(3-aminobutylamide)-4-(trifluoromethyl)-phenyl]nicotinamide hydrochloride

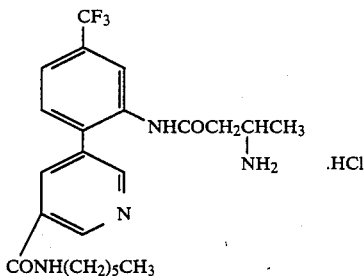

Colorless scales
Melting point: 136°–142° C.
NMR(CD$_3$OD) δ: 0.8–1.9 (14H, m, (CH$_2$)$_4$CH$_3$, CH$_3$); 2.66 (2H, d, J=6 Hz, COCH$_2$); 3.3–3.8 (3H, m, NHCH$_2$, CH); 7.7–7.9 (2H, m, aromatic H); 8.03 (1H, d, J=2 Hz, aromatic H); 8.40 (1H, m, aromatic H); 8.82 (1H, m, aromatic H); 9.10 (1H, m, aromatic H).
IR $\nu_{max}^{KBr}$ cm$^{-1}$: 3207, 1635.

EXAMPLE 51

Methyl 5-[2-(3-aminobutyramide)-4-(trifluoromethyl)phenyl]-nicotinate monohydrochloride Colorless fine needles
Melting point: 193°–196° C. (ethanol-ether)
NMR(CD$_3$OD) δ: 1.29 (3H, d, J=7 Hz, CH$_3$); 2.64 (2H, d, J=6 Hz, COCH$_2$); 3.45–3.78 (1H, m, CH); 4.03 (3H, s, COOCH$_3$); 7.60–7.88 (2H, m, aromatic H); 8.02 (1H, d, J=2 Hz, aromatic H); 8.48 (1H, m, aromatic H); 8.87 (1H, m, aromatic H); 9.23 (1H, m, aromatic H).
IR $_{max}^{KBr}$ cm$^{-1}$: 3403, 3182, 1717, 1668.

EXAMPLE 52

3-Amino-2'-methoxy-5'-nicotinoylbutyranilide hydrochloride

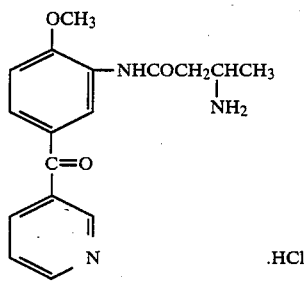

(1) 6.4 g of 3-(4-methoxybenzoyl)pyridine obtained by reacting nicotinoyl chloride hydrochloride with anisole was nitrated by the same treatment as in Example 47, (3) to give 7.3 g (yield 94%) of 3-(4-methoxy-3-nitrobenzoyl)pyridine as pale yellow needles having a melting point of 86° to 88° C.

(2) The resulting compound was aminated and amidated by the same treatment as in Example 1, and the product was recrystallized from ethanol-ether to give 3-amino-2'-methoxy-5'-nicotinoylbutyranilide hydrochloride as colorless fine needles having a melting point of 223° to 226° C.

NMR(CD$_3$OD) δ: 1.42 (3H, d, J=7 Hz, CH$_3$); 2.86 (2H, d, J=6 Hz, COCH$_2$); 3.51–3.88 (1H, m, CH); 4.03 (3H, s, OCH ); 7.21 (1H, d, J=9 Hz, aromatic H); 7.56–7.80 (2H, m, aromatic H); 8.24 (1H, m, aromatic H); 8.66 (1H, d, J=2 Hz, aromatic H); 8.82 (1H, m, aromatic H); 8.90–9.04 (1H, m, aromatic H).
IR $\nu_{max}^{KBr}$ cm$^{-1}$: 3399, 3226, 1679, 1657.

EXAMPLES 53–55

The following compounds were produced by performing the same procedure as in Example 52.

EXAMPLE 53

3-Amino-2'-methyl-5'-nicotinoyl butyranilide hydrochloride

Pale yellow amorphous compound
NMR(CD$_3$OD) δ: 1.46 (3H, d, J=7 Hz, CH$_3$); 2.41 (3H, s, CH$_3$); 2.93 (2H, d, J=6 Hz, COCH$_2$); 3.53–3.92 (1H, m, CH); 7.12–7.94 (3H, m, aromatic H); 8.07 (1H, d, J=2 Hz, aromatic H); 8.27 (1H, m, aromatic H); 8.86 (1H, m, aromatic H); 8.99 (1H, m, aromatic H).
IR $\nu_{max}^{KBr}$ cm$^{-1}$: 3406, 1651.

EXAMPLE 54

Ethyl 3-[3-(3-aminobutyramide)-4-methoxybenzoyl]-2-pyridinecarboxylate hydrochloride Colorless fine needles
Melting point: 140°–143° C.
NMR(CD$_3$OD) δ: 1.14 (3H, t, J=8 Hz, CH$_3$); 1.41 (3H, d, J=7 Hz, CH$_3$); 2.85 (2H, d, J=6 Hz, COCH$_2$); 3.53–3.87 (1H, m, CH); 4.01 (3H, s, OCH$_3$); 4.19 (2H, q, COOCH$_2$CH$_3$); 7.19 (1H, d, J=9 Hz, aromatic H); 7.57

(1H, d,d, J=2, 9 Hz, aromatic H); 7.79 (1H, m, aromatic H); 8.03 (1H, m, aromatic H); 8.65 (1H, d, J=2 Hz, aromatic H); 8.87 (1H, m, aromatic H).

IR $\nu_{max}^{KBr}$ cm$^{-1}$: 3388, 1710, 1660.

EXAMPLE 55

Ethyl 3-[3-(2-aminopropionamide)-4-methoxybenzoyl]-2-pyridinecarboxylate hydrochloride Colorless fine needles Melting point: 161°–166° C.

NMR(CD$_3$OD) δ: 1.34 (3H, t, J=9 Hz, CH$_3$); 1.63 (3H, d, J=7 Hz, CH$_3$); 3.96–4.46 (6H, m, OCH$_3$, COOCH$_2$CH$_3$, CH); 7.20 (1H, d, J=9 Hz, aromatic H); 7.61 (1H, d,d, J=2, 9 Hz, aromatic H); 7.82 (1H, m, aromatic H); 8.03 (1H, m, aromatic H); 8.63 (1H, d, J=2 Hz, aromatic H); 8.80 (1H, m, aromatic H).

IR $\nu_{max}^{KBr}$ cm$^{-1}$: 3398, 1720, 1693, 1653.

EXAMPLE 56

3-Amino-5'-[hydroxy-(3-pyridyl)methyl]-2'-methoxybutyranilide hydrochloride

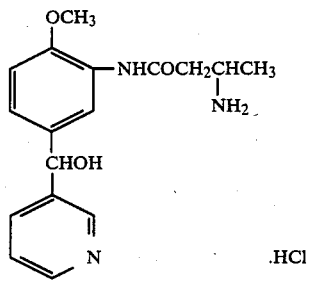

(1) 283 mg of 3-(t-butoxycarbonylamino)-5'-nicotinoyl-3'-methoxybutyranilide obtained as an intermediate in Example 52 was dissolved in 8 mg of diglyme, and 76 mg of sodium borohydride was added. The mixture was heated under reflux for 6 hours. The reaction solution was extracted with ethyl acetate and washed with water. The solvent was evaporated. The residue was purified by preparative silica gel thin-layer chromatography (developing solvent: chloroform-methanol=95/5) to give 123 mg (yield 43%) of 3-(t-butoxycarbonylamino)-5'-[hydroxy-(3-pyridyl)methyl]-2'-methoxybutyranilide as an oil.

The compound was then de-t-butoxycarbonylated by the same treatment as in Example 1 to give 3-amino-5'-hydroxy-(3-pyridyl)methyl]-2'-methoxybutyranilide hydrochloride.

NMR(CD$_3$OD) δ: 1.38 (3H, d, J=7 Hz, CH$_3$); 2.83 (2H, d, J=6 Hz, COCH$_2$); 3.54–3.83 (1H, m, CH); 3.88 (3H, s, OCH$_3$); 5.83 (1H, s, CH(OH)); 7.00 (1H, d, J=8 Hz, aromatic H); 7.21 (1H, d,d, J=2, 8 Hz, aromatic H); 7.43 (1H, m, aromatic H); 7.92 (1H, m, aromatic H); 8.12 (1H, d, J=2 Hz, aromatic H); 8.45 (1H, m, aromatic H); 8.62 (1H, m, aromatic H).

IR $\nu_{max}^{KBr}$ cm$^{-1}$: 3363, 1661.

EXAMPLE 57

3-Amino-5'-(4-pyridylmethyl)-2'-(2,2,2-trifluoroethoxy)butyranilide hydrochloride

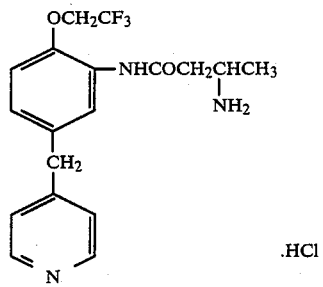

(1) 3.0 g of diisopropyl-1-ethoxycarbonyl-1,4-dihydropyridine-4-phosphonate was dissolved in 50 ml of tetrahydrofuran. The solution was cooled to −78° C. with a dry ice-acetone freezing mixture. In a stream of nitrogen, 6.8 ml of a hexane solution of n-butyllithium was slowly added dropwise. A solution of 2.50 g of p-bromobenzyl bromide in 10 ml of tetrahydrofuran was added dropwise. The temperature of the solution was returned to room temperature, and the solution was stirred for 20 hours. The excess of n-butyllithium was decomposed with ammonium chloride, and the solvent was evaporated. The residue was extracted with ethyl acetate. The extract was washed with a saturated aqueous solution of sodium hydrogen carbonate, a saturated aqueous solution of sodium thiosulfate and a saturated aqueous solution of sodium chloride in this order, and the solvent was evaporated. The residue was subjected to silica gel column chromatography. The column was eluted with a 1:9 mixture of acetone and benzene to give 2.76 g (yield 56.6%) of diisopropyl-4-(4-bromobenzyl)-1-ethoxycarbonyl-1,4-dihydropyridine-4-phosphonate as a brown oil.

(2) 2 ml of chlorotrimethylsilane was added to 2.76 g of the resulting compound and a solution of 4.2 g of sodium iodide in 50 ml of acetonitrile. In a stream of nitrogen, the mixture was stirred at a bath temperature of 80° to 90° C. After the reaction, the reaction mixture was filtered. The solvent was evaporated from the filtrate, and the residue was extracted with ethyl acetate. The extract was washed with a 1N aqueous solution of sodium hydroxide and a saturated aqueous solution of sodium chloride in this order. The solvent was evaporated to give 922 mg (yield 65.6%) of 4-(4-bromobenzyl)pyridine.

(3) In a stream of nitrogen, 2.0 ml of 2,2,2-trifluoroethanol was added to 52.8 mg of sodium hydride, and then a solution of 140 mg of copper iodide and 922 mg of 4-(4-bromobenzyl)pyridine in 4 ml of N,N'-dimethylformamide was added. The mixture was stirred at a bath temperature of 120° C. for 3 hours. After the reaction, water was added to the reaction mixture, and it was extracted with ethyl acetate. The extract was washed with water, and the solvent was evaporated. 0.78 g of the residue was distilled under reduced pressure by using a Kugel-Rohr. When 574 mg (yield 57%) of a fraction having a boiling point of 150° C. (0.2 mmHg) was separated, 4-[4-(2,2,2-trifluoroethoxy)benzyl]pyridine was obtained as colorless crystals having a melting point of 51° to 53° C.

(4) The resulting compound was nitrated by the same procedure as in Example 47, (3) and reduced and amidated by the same procedure as in Example 1 to give 3-amino-5'-(4-pyridylmethyl)-2'-(2,2,2-trifluoroethoxy)-butyranilide hydrochloride as colorless crystals having a melting point of 231° to 234° C.

NMR(CD$_3$OD) δ: 1.41 (3H, d, J=7 Hz, CH$_3$); 2.81 (2H, d, J=61 Hz, COCH$_2$); 3.56–3.84 (1H, m, CH); 4.18 (2H, s, CH$_2$); 4.63 (2H, q, J=8 Hz, OCH$_2$CF$_3$); 7.16 (2H, s, aromatic H); 7.63–7.80 (2H, m, aromatic H); 7.82 (1H, s, aromatic H); 8.48–8.80 (2H, m, aromatic H).

IR $\nu_{max}^{KBR}$ cm$^{-1}$: 3407, 1657, 1597, 1544, 1437.

EXAMPLE 58

By performing the same procedure as in Example 57, 3-amino-5'-(2-pyridylmethyl)-2'-(2,2,2-trifluoroethoxy)-butyranilide dihydrochloride was obtained.

Pale brown crystals

Melting points: 128°–130° C.

NMR(CD$_3$OD) δ: 1.39 (3H, d, J=7 Hz, CH$_3$); 2.82 (2H, d, J=6 Hz, COCH$_2$); 3.54–3.88 (1H, m, CH); 4.46 (2H, s,

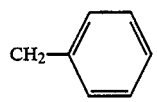

); 4.64 (2H, q, J=8 Hz, OCH$_2$CF$_3$); 7.22 (2H, m, aromatic H); 7.76–8.11 (3H, m, aromatic H); 8.26–8.72 (1H, m, aromatic H); 8.74–8.96 (1H, m, aromatic H).

IR $\nu_{max}^{KBr}$ cm$^{-1}$: 3406, 1651, 1614.

EXAMPLE 59

3-Amino-5'-methoxy-2'-(4-pyridylthio)butyranilide

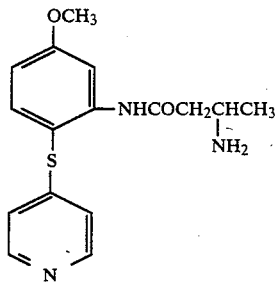

(1) 1.11 g of 4-mercaptopyridine was dissolved in 5 ml of ethanol, and 52.8 mg of sodium hydride was added little by little. The mixture was stirred for 5 minutes, and then a solution of 1.87 g of 4-chloro-3-nitroanisole in 5 ml of dioxane was added. The mixture was heated under reflux at 100° C. for 15 hours. The solvent was evaporated, and 2N hydrochloric acid was added to the residue. The residue was washed with ether, made alkaline by adding an aqueous solution of sodium hydroxide, and extracted with methylene chloride. The extract was washed with a saturated aqueous solution of sodium chloride. The solvent was evaporated. The resulting residue was subjected to silica gel column chromatography. The column was eluted with a 5:3 mixture of hexane and acetone, and the eluate was recrystallized from acetone-hexane to give 562 mg (yield 21.4%) of 4-(4-methoxy-2-nitrophenyl)thiopyridine as orange needles having a melting point of 57° to 59° C.

(2) 536 mg of the resulting compound was dissolved in a mixture of 7 ml of toluene and 7 ml of methanol, and while the solution was heated under reflux, 336 mg of sodium hydrosulfide was added dropwise over 10 minutes. The mixture was heated under reflux for 4 hours. The precipitate was removed by filtration, and the solvent was evaporated from the filtrate. The residue was dissolved in 6N hydrochloric acid and washed with methylene chloride. The aqueous layer was made alkaline with concentrated aqueous ammonia and extracted with methylene chloride. The extract was washed with a saturated aqueous solution of sodium chloride. The solvent was then evaporated. The solvent was evaporated, and purified by preparative silica gel thin-layer chromatography (developing solvent: hexane/acetone=5/3). The purified product was recrystallized from methylene chloride-hexane to give mg (yield 60.5%) of 4-(2-amino-4-methoxyphenyl)thiopyridine as pale yellow needles having a melting point of 93° to 94° C.

(3) The product was then worked up as in Example 1 to give 3-amino-5'-methoxy-2'-(4-pyridylthio)butyranilie as a brown oil.

NMR(CDCl$_3$) δ: 1.05 (3H, d, J=7 Hz, CH$_3$); 1.33 (2H, br.s, NH$_2$); 2.1–2.52 (2H, m, COCH$_2$); 3.02–3.31 (1H, m, CH); 3.90 (3H, s, OCH$_3$); 6.74 (1H, d,d, J=2,9 Hz, aromatic H); 6.80–6.98 (2H, m, aromatc H); 7.50 (1H, d, J=9 Hz, aromatic H); 8.29–8.45 (3H, m, aromatic H).

IR $\nu_{max}^{film}$ cm$^{-1}$: 3361, 3006, 2950, 1671.

Mass m/e: 317 (M+)

EXAMPLES 60–63

The following compounds were produced by the same procedure as in Example 59.

EXAMPLE 60

3-Amino-5'-(octyloxy)-2'-(3-pyridyl)butyranilide dihydrochloride

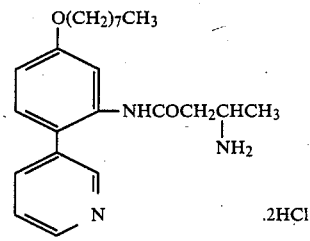

Pale yellow needles

Melting point: 179°–181° C. (decomp.) (ethanol-hexane)

EXAMPLE 61

3-Amino-5'-(4-methyl-1-pentyloxy)-2'-(3-pyridyl)-butyranilide dihydrochloride

Pale yellow needles

Melting point 208°–210° C. (decomp.)(ethanol-hexane)

EXAMPLE 62

3-Amino-5'-(tetradecyloxy)-2'-(3-pyridyl)butyranilide dihydrochloride

Colorless needles

Melting point: 160°–162° C. (decomp.)(methanol-ether)

EXAMPLE 63

4-Amino-5'-(ethoxy)-2'-(3-pyridyl)butyranilide dihydrochloride

Pale yellow needles

Melting point: 170°–172° C. (decomp.)(ethanol/n-hexane)

Examples of formulating pharmaceutical preparation containing the compound of this invention are shown below.

Example A: tablet

|  | A | B |
|---|---|---|
| Compound (I) or its salt | 50 mg | 100 mg |
| Lactose | 61.5 | 90.5 |
| Crystalline cellulose | 22 | 37 |
| Hydroxypropyl cellulose having a low degree of substitution | 115 | 20 |
| Magnesium stearate | 1.5 | 2.5 |
| Total (per tablet) | 150 mg | 250 mg |

The above ingredients were tableted in a customary manner to form tablets.

Example B: capsules

|  | A | B |
|---|---|---|
| Compound (I) or its salt | 50 mg | 100 mg |
| Corn starch | 40 | 30 |
| Crystalline cellulose | 60 | 30 |
| Talc | 30 | 20 |
| Total (per capsule) | 180 mg | 180 mg |

The above ingredients were filled in #3 gelatin capsules to form capsular agents.

Example C: injectable preparation

|  | A | B |
|---|---|---|
| Compound (II) or its salt | 12.5 mg | 12.5 mg |
| Sodium chloride | 14.0 | 14.0 |
| Mannitol | 100.0 | 100.0 |
| Disodium phosphate 12-hydrate | 10.72 | 10.72 |
| Monosodium phosphate 2-hydrate | 4.68 | 4.68 |

The above ingredients were dissolved in injectable distilled water, and the solution was sterilized and filtered through a membrane filter, and put in sterilized vials in an amount of 2 ml each. It was lyophilized under the following conditions, and stopped with a rubber stopper after nitrogen substitution to prepare an injectable preparation to be melted prior to use.

| Lyophilization conditions | |
|---|---|
| Pre-lyophilization: −40° C. | more than 3 hours |
| First drying: −40° C. to +10° C. | more than 15 hours |
| Second drying: +10° C. to +60° C. | more than 5 hours |
| Third drying: +50° C. | more than 2 hours |

What we claim is:

1. A substituted anilide derivative of the formula

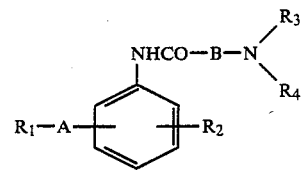

wherein
R$_1$ represents a pyridyl group,
R$_2$ represents a hydrogen atom, a halogen atom, a lower alkyl group, a trifluoromethyl group, a lower alkenyloxy group, a trifluoroethoxy group or a C$_1$–C$_{14}$ alkoxy group,
R$_3$ and R$_4$ are identical or different, and each represents a hydrogen atom or a lower alkyl group, and
B represents a lower alkylene group, or an acid/addition salt thereof.

2. The compound of claim 1 wherein R$_2$ is a lower alkyl group, an allyloxy group, a lower alkoxy group, or a 2,2,2-trifluoroethoxy group.

3. The compound of claim 1 wherein R$_2$ is a lower alkoxy group.

4. The compound of claim 1 wherein R$_3$ and R$_4$ are both hydrogen atoms.

5. The compound of claim 1 wherein B is a linear or branched lower alkylene group.

6. The compound of claim 1 wherein B is

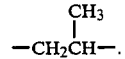

7. The compound of claim 1 wherein the group R$_1$ R$_2$- each exist at an ortho- or meta-position to the group

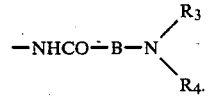

8. The compound of claim 1 wherein the group R$_1$ exists at a para-position to the group R$_2$-.

9. 3-Amino-5'-ethoxy-2'-(3-pyridyl)butyranilide and its pharmaceutically acceptable acid addition salt.

10. 3-Amino-5'-allyloxy-2'-(3-pyridyl)butyranilide and its pharmaceutically acceptable acid addition salt.

11. A pharmaceutical composition for the control and prevention of arrhythmia comprising an effective amount of a compound of formula (I) in claim 1 or a pharmaceutically acceptable diluent or carrier.

12. A method for treating arrhythmia in an individual which comprises administering an effective amount of a compound of formula (I) in claim 1 or a pharmaceutically acceptable salt thereof to an individual.

* * * * *